United States Patent
Jiang

(10) Patent No.: US 9,700,258 B2
(45) Date of Patent: Jul. 11, 2017

(54) APPARATUS FOR SENSING AND MEASURING PRESSURE AND SHEAR COMPONENTS OF A FORCE AT AN INTERFACE BETWEEN TWO SURFACES

(71) Applicant: University of Southampton, Southampton (GB)

(72) Inventor: Liudi Jiang, Southampton (GB)

(73) Assignee: University of Southampton, Southampton (GB)

(*) Notice: Subject to any disclaimer, the term of this patent is extended or adjusted under 35 U.S.C. 154(b) by 0 days.

(21) Appl. No.: 14/392,042

(22) PCT Filed: Oct. 31, 2013

(86) PCT No.: PCT/GB2013/000465
§ 371 (c)(1),
(2) Date: Apr. 29, 2015

(87) PCT Pub. No.: WO2014/068269
PCT Pub. Date: May 8, 2014

(65) Prior Publication Data
US 2016/0015311 A1    Jan. 21, 2016

(30) Foreign Application Priority Data

Oct. 31, 2012 (GB) .................................. 1219632.5

(51) Int. Cl.
*A61B 5/00* (2006.01)
*A61F 2/80* (2006.01)
(Continued)

(52) U.S. Cl.
CPC ............ *A61B 5/447* (2013.01); *A61B 5/6807* (2013.01); *A61B 5/6892* (2013.01);
(Continued)

(58) Field of Classification Search
CPC ... A61B 5/447; A61B 5/68942; A61B 5/6892; A61B 5/6807; A61B 5/6894; A61F 2/80;
(Continued)

(56) References Cited

U.S. PATENT DOCUMENTS

| 4,836,033 A | 6/1989 | Seitz |
| 5,343,765 A * | 9/1994 | Okada ..................... G01L 5/165 73/862.043 |

(Continued)

FOREIGN PATENT DOCUMENTS

| EP | 0 742 597 A1 | 11/1996 |
| EP | 1 935 379 A2 | 6/2008 |

(Continued)

*Primary Examiner* — Lisa Caputo
*Assistant Examiner* — Philip Cotey
(74) *Attorney, Agent, or Firm* — Iandiorio Teska & Coleman, LLP

(57) ABSTRACT

Apparatus (2) for sensing and measuring and/or shear components of a force at an interface between two surfaces, which apparatus (2) comprises: (i) at least one flexible means (4) for receiving the pressure and/or shear components of the force; and (ii) transducer means (6) for producing electrical signals consequent upon movement of the flexible means (4) in response to the pressure and/or shear components of the force, and the apparatus (2) being such that: (iii) the flexible means (4) comprises first and second electrode parts (18, 20) which are spaced apart by the flexible means (12); (iv) the first and second electrode parts (18, 20) move solely towards each other as a result of the pressure component of the force being applied to the flexible means (4); and (v) the first and second electrode parts (18, 20) move towards and parallel to each other as a result of the shear component of the force being applied to the flexible means (4).

23 Claims, 14 Drawing Sheets

(51) Int. Cl.
  *G01L 1/12* (2006.01)
  *G01L 1/14* (2006.01)
  *G01L 5/16* (2006.01)
  *A61F 2/76* (2006.01)
  *A61F 2/78* (2006.01)
  *A61F 2/70* (2006.01)
  *A61G 7/057* (2006.01)

(52) U.S. Cl.
  CPC .............. *A61B 5/6894* (2013.01); *A61F 2/70* (2013.01); *A61F 2/76* (2013.01); *A61F 2/7812* (2013.01); *A61F 2/80* (2013.01); *G01L 1/127* (2013.01); *G01L 1/146* (2013.01); *G01L 5/164* (2013.01); *G01L 5/165* (2013.01); *A61F 2002/7635* (2013.01); *A61F 2002/785* (2013.01); *A61G 7/057* (2013.01); *A61G 2203/32* (2013.01)

(58) Field of Classification Search
  CPC ........ A61F 2/70; A61F 2002/785; A61F 2/76; A61F 2/7812; A61F 2002/7635; G01L 1/127; G01L 1/146; G01L 5/164; G01L 5/165; A61G 2203/32; A61G 7/057
  See application file for complete search history.

(56) References Cited

U.S. PATENT DOCUMENTS

| | | | | |
|---|---|---|---|---|
| 5,571,973 A | * | 11/1996 | Taylot | A61B 5/1036 73/862.046 |
| 2005/0000298 A1 | | 1/2005 | Pfeifer et al. | |
| 2005/0004500 A1 | * | 1/2005 | Rosser | A61B 5/447 602/41 |
| 2005/0148904 A1 | * | 7/2005 | Mimura | A61B 5/1126 600/587 |
| 2005/0232532 A1 | * | 10/2005 | Wang | A61B 5/6892 385/13 |
| 2005/0241409 A1 | * | 11/2005 | Taylor | A61B 5/103 73/841 |
| 2008/0262341 A1 | * | 10/2008 | Boyden | A61F 2/02 600/424 |
| 2009/0031825 A1 | | 2/2009 | Kishida et al. | |
| 2010/0162832 A1 | * | 7/2010 | Brauers | A61B 5/103 73/862.626 |
| 2011/0068939 A1 | * | 3/2011 | Lachenbruch | A61B 5/002 340/626 |
| 2011/0193363 A1 | * | 8/2011 | Nishiwaki | B25J 13/083 294/86.4 |
| 2011/0213221 A1 | * | 9/2011 | Roche | A61B 5/0031 600/301 |
| 2011/0221457 A1 | | 9/2011 | Takahashi et al. | |
| 2011/0263950 A1 | * | 10/2011 | Larson | A61B 5/024 600/301 |
| 2012/0293491 A1 | * | 11/2012 | Wang | G06F 3/0338 345/419 |
| 2013/0079693 A1 | * | 3/2013 | Ranky | H01L 41/314 602/28 |
| 2013/0234734 A1 | * | 9/2013 | Iida | G06F 3/044 324/661 |

FOREIGN PATENT DOCUMENTS

| | | |
|---|---|---|
| EP | 2 042 847 A1 | 4/2009 |
| JP | 2003337071 A | 11/2003 |
| JP | 2010122018 A | 6/2010 |
| WO | WO 2008/042903 A2 | 4/2008 |
| WO | WO 2008/102308 A2 | 8/2008 |
| WO | WO 2009/120270 A2 | 10/2009 |

* cited by examiner

APPARATUS FOR SENSING AND MEASURING PRESSURE AND SHEAR COMPONENTS OF A FORCE AT AN INTERFACE BETWEEN TWO SURFACES

This invention relates to apparatus for sensing pressure and shear components of a force, and more especially this invention relates to apparatus for sensing and measuring pressure and shear components of a force at an interface between two surfaces.

It is known to provide flexible sensor apparatus at the interface between two surfaces such for example as between a part of a human body and an external support surface in order to provide mapping information. Such known sensor apparatus is however only able to measure the pressure component of a force, which acts perpendicular to one of the surfaces, for example the part of the human body. The known sensor apparatus is not able to measure the shear component of a force which acts parallel to the surface.

Both pressure and shear components of a force exist at the interface between a part of a human body and an external support surface. Excessive exposure to pressure and shear components of a force is an important factor causing damage to the part of the human body. The damage may be, for example, skin tissue breakdowns leading to skin ulcers. The problem is especially acute when the external support surface is a prosthesis. The problem is also severe when the external support surface is a wheelchair, a bed or an article of footwear.

The above mentioned problem is a long-standing problem and one which is well known in the medical field. In spite of this and also in spite of the severe discomfort caused to many people such for example as amputees, diabetics and elderly patients, the problem still exists.

The present invention is based on the realisation that the shear component of a force is at least as important, if not more important, than the pressure component of a force in causing skin tissue breakdowns such for example as ulcers. If the above problem is to be met, it is firstly necessary to be able to measure the pressure and shear components of a force at the interface between the part of the human body and the external support surface. In addition, any such apparatus able to provide the required measurements must be of a design which is comfortable for wear since the apparatus will be in contact with the human body. Still further, the apparatus needs to be able to be produced in a cost-effective and commercial manner.

Accordingly, the present invention provides apparatus for sensing and measuring pressure and shear components of a force at an interface between two surfaces, which apparatus comprises:
 (i) at least one flexible means for receiving the pressure component of the force and the shear component of the force; and
 (ii) transducer means for producing electrical signals consequent upon movement of the flexible means in response to the pressure component of the force and/or the shear component of the force,
and the apparatus being such that:
 (iii) the transducer means comprises first and second electrode parts which are spaced apart by the flexible means;
 (iv) the first and second electrode parts move solely towards each other as a result of the pressure component of the force being applied to the flexible means;
 (v) the first and second electrode parts move towards and parallel to each other as a result of the shear component of the force being applied to the flexible means; and
 (vi) the movement of the first and second electrode parts towards and parallel to each other is such that:
  (a) the movement has an X-direction component due to the shear component of the force having an X-direction; and
  (b) the movement has a Y-direction component due to the shear component of the force having a Y-direction.

The apparatus of the present invention is advantageous in that it is able to measure the pressure and/or the shear components of a force at the interface between the two surfaces. This enables hitherto unevaluated shear forces to be evaluated and taken into account in providing appropriate apparatus for location at the interface between the two surfaces. In the case of the two surfaces being a part of the human body and an external support surface, the apparatus of the present invention is advantageous in that the transducer means with its first and second electrode parts spaced apart by the flexible means is able to be a user-friendly structure which is comfortable for use, and does not cause unnecessary discomfort to a person when the apparatus is installed at the interface between the part of the human body and the external support surface.

The apparatus of the present invention may be one that has been produced by 3D printing using a 3D printer, and/or by elastomer material which is moulded to shape. The 3D printing using a 3D printer may enable the 3D printed flexible means to be produced in a cost-effective manner, whereby high manufacturing costs do not prevent the commercialisation of the apparatus. The flexible means may be obtained using input data from scanning of a body part such for example as a prosthetic stump.

The apparatus of the present invention may be integral with at least one sensing pad for use within a prosthetic socket liner or a prosthetic socket.

The apparatus of the present invention may be produced by 3D printing, additive manufacturing or rapid phototyping. Commercially available 3D printers are able to print out designed 3D structures rapidly at a low cost. Feature resolution is fast improving. For example 3D printers with fine resolution features of approximately 30 μm are now commercially available 3D printers can also print out structures of a wide variety of shapes, including planar and curved shaped.

The flexible means used in the apparatus of the present invention can be produced to accommodate a wide variety of surface shapes for locating at the external support surface. The production processes that are employed can be adapted to operate using data obtained using CAD technology.

The apparatus of the present invention may be one in which at least one of the first and second electrode parts has a planar surface. Alternatively, the apparatus of the present invention may be one in which at least one of the first and second electrode parts has a non-planar surface.

The apparatus of the present invention may be one in which the first and second electrode parts are flexible or rigid. The apparatus may be one in which at least one of the first and second electrode parts includes at least one flexible printed circuit board.

The flexible means may be made of a plastics material, another type of polymer material, a textile, an elastomer, a prosthetic socket liner material, a 3D printing material, or any other suitable type of material. The prosthetic socket liner material may be, for example, silicone, a thermoplastic elastomer, or urethane.

The apparatus of the present invention may be one in which the flexible means has planar or non-planar surfaces. A wide variety of structures for the flexible means may be employed. The use of the non-planar surfaces may enable surface-contour fitting.

The apparatus of the present invention may be one in which the flexible means is an insulating sensing structure, and in which the transducer means comprises conductive layers which are provided on the flexible means and which enable the production of an electrical signal. The conductive layers may be provided on the insulating sensing structure in any suitable way, for example by attachment or by deposition.

The flexible means may be a single flexible spacer means. Alternatively the flexible means may be a plurality of separate flexible members. The flexible means may have end contacting members, for example in the form of face plates. Other types of flexible means may be employed.

The plurality of separate flexible members may be flexible pillar members. Constructions other than flexible pillar members may be employed. The flexible pillar members are preferably of circular cross section. Other cross sectional shapes may be employed including, for example, square, rectangular and octagonal cross sectional shapes.

The flexible means can have any suitable three dimensional shape for example, columns, filleted shapes, helical coil shapes, pyramids, pillars, tilted pillars etc.

The flexible means may be empty flexible members with flexible sidewalls. The flexible members may be filled with a compliant material or a combination of different compliant materials.

Space between the flexible members may be filled with a compliant material or a combination of different compliant materials.

When the flexible means is in the form of a solid continuous member, then the solid continuous member may be made of a compliant material or a combination of different compliant materials. The compliant material may be a gel material or a combination of different gel materials. The compliant material may be a polymer material or a combination of different polymer materials. Other compliant materials may be employed, for example powdered materials.

The apparatus of the present invention may be one in which the transducer means is a capacitive transducer means.

The capacitive transducer means may comprise a first capacitive member on a first surface of the flexible means, and a second capacitive member on a second surface of the flexible means. The first capacitive member may be a member with planar or non-planar surfaces, and may contain multiple electrodes. Other constructions for the first capacitive member may be employed. The second capacitive member may be a member with planar or non-planar surfaces, and may contain multiple electrodes. Other constructions for the second capacitive member may be employed. The first and second capacitive members may be the same or different.

Alternatively, the apparatus of the present invention may be one in which the transducer means is an inductive transducer means.

The inductive transducer means may comprise a first inductive member on a first surface of the flexible means, and a second inductive member on a second surface of the flexible means. The first inductive member may be a coil. Other formations for the first inductive member may be employed. The second inductive member may be a coil. Other constructions for the second inductive member may be employed. The first and second inductive members may be the same or different.

The apparatus of the present invention may include at least one signal processing integrated circuit. The signal processing circuit or circuits are preferably implemented by integrated circuit chips which can be embedded, inserted or assembled into the apparatus. The signal processing circuitry can be produced by using 3D printing, ink jet printing, or by other means if desired.

The apparatus of the present invention may include a plurality of the flexible means. The flexible means may form a regular or irregular array. The flexible means may be planar and/or non-planar.

The present invention also extends to an article when provided with the apparatus of the invention. The article may be, for example, a prosthesis, a wheelchair, a bed, or footwear. The bed may be a hospital bed. The footwear may be such that the apparatus of the present invention is installed in an insole and/or outer sole and/or shell in the footwear.

The article may be one which is in the form of a prosthesis, and in which the apparatus is in the form of a prosthetic socket liner.

The article may be one which is in the form of the prosthesis, and in which the apparatus is in the form of one or more sensing pads in a prosthetic socket of the prosthesis.

The article may include a closed loop control system for activating relevant actuators in response to signals from the apparatus of the present invention.

The apparatus of the present invention may be produced such that electrical signals associated with the pressure and shear components of the force are not only separately detected, but they are able to be associated for control purposes, with minimal signal cross talking. As indicated above, the sensor signals can be used to trigger actuators to modulate relevant functions of the apparatus, for example for biomedical use.

Embodiments of the invention will now be described solely by way of example and with reference to the accompanying drawings in which:

FIG. 1b is an underneath plan view of the apparatus shown in FIG. 1a;

FIG. 2b is an underneath plan view of the apparatus shown in FIG. 2a;

FIG. 3b is a cross section on the line 3-3 shown in FIG. 3a;

FIG. 4b is a cross section on the line 4-4 shown in FIG. 4a;

Figure 1A:
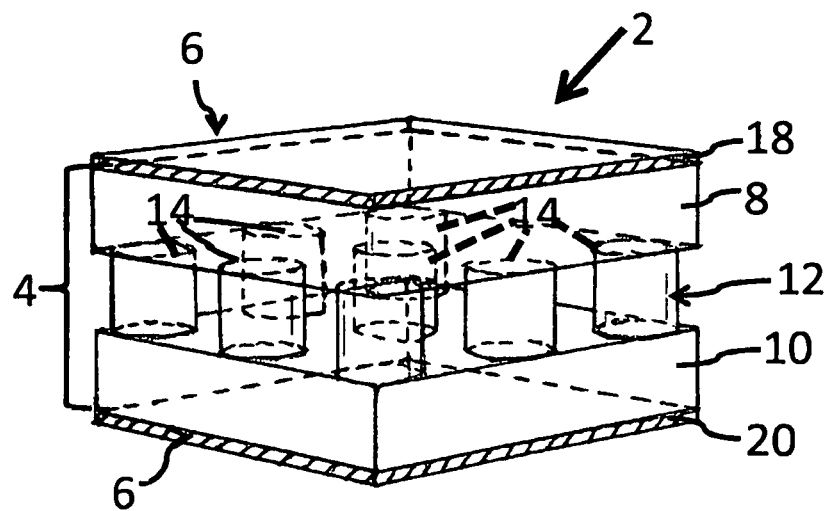
FIG. 1a is a perspective view of part of first apparatus of the present invention.

Referring to FIG. 1a, there is shown apparatus 2 for sensing and measuring pressure and/or shear components of a force at an interface between two surfaces such for example as between a part of a human body and an external support surface. The apparatus 2 comprises flexible means 4 for sensing the pressure and/or shear components of the force. The apparatus 2 further comprises transducer means 6 for producing electrical signals consequent upon movement of the flexible means 4 in response to the pressure and/or shear components of the force.

The apparatus 2 is such that the flexible means 4 comprises a first part 8 and a second part 10. The first and second parts 8, 10 are spaced apart by inner flexible means 12. The first and second parts 8, 10 may be regarded as contacting or face parts of the flexible means 4.

The first and second parts 8, 10 move solely towards each other as a result of the pressure component of the force being applied to the flexible means 4. The first and second parts 8, 10 move towards and parallel to each other as a result of the shear component of the force being applied to the flexible means 4.

The flexible means 4 may be one that has been produced by 3D printing using a 3D printer. Alternatively, the flexible means 4 may be one that has been produced using elastomer material which has been moulded to shape.

As can be appreciated from FIG. 1a, the first part 8 is a plate which can be planar or non planar. The second part 10 is also a plate which can be planar or non-planar. The first and second parts 8, 10 may be flexible or rigid.

Figure 1B:
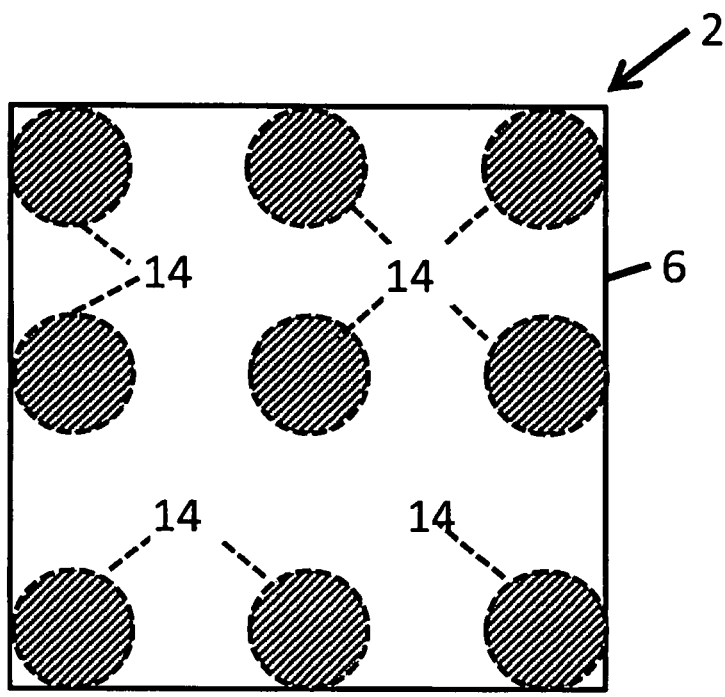
Figure 1C:
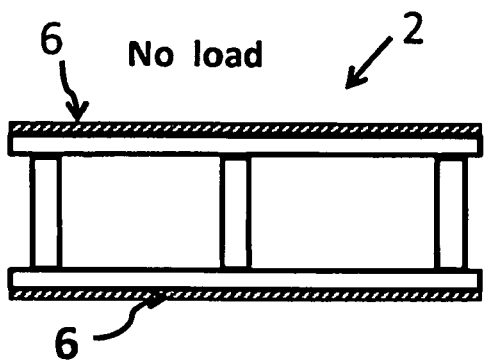
FIG. 1c is a schematic edge view of the apparatus shown in FIG. 1a when not subject to a force in the form of a load.

The inner flexible means 12 is a plurality of flexible members 14. The cross section of the flexible members 14 can be of any shape, for example round, circular, elliptical, square, rectangular or octagonal cross sectional shapes. Each flexible member 14 can have the same or different cross sectional shapes. The flexible members 14 can have any suitable shapes, for example columns, filleted shapes, helical coil shapes, pyramids, pillars, or tilted pillars. Each flexible member 14 can have the same or a different shape. The flexible members 14 are made from polymer materials. The flexible members 14 are solid flexible pillars as can best be seen from FIG. 1b.

The transducer means 6 is a capacitive transducer means 6. More specifically, the capacitive transducer means 6 comprises a first capacitive member 18 on a first surface of the flexible means 4, and a second capacitive member 20 on a second surface of the flexible means 4. The first capacitive member 18 is a planar member in the form of a plate, and it is on the first part 8. The second capacitive member 20 is a planar member in the form of a plate, and it is on the second part 10.

Figure 1D:
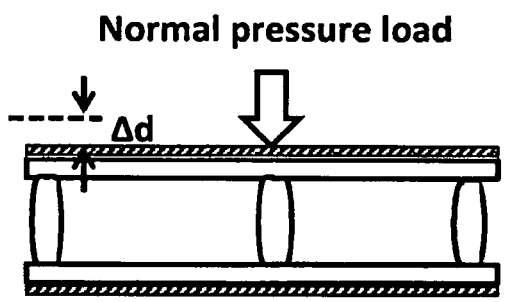
FIG. 1d is a schematic edge view of the apparatus shown in FIG. 1a and when subject to a pressure force, the pressure force being perpendicular to one of two contacting surfaces, and the pressure force being in the form of a direct pressure load.
Figure 1E:
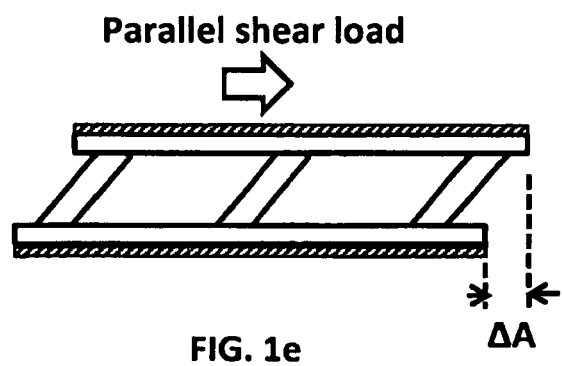
FIG. 1e is a schematic edge view of the apparatus shown in FIG. 1a when subject to a shear force, the shear force being parallel to one of two contacting surfaces, and the shear force being in the form of a parallel direction shear load.

When the apparatus 2 is in use and is subjected to a force of arbitrary direction, the force can be decomposed into a pressure component which is normal, i.e. perpendicular, to one of the surfaces such for example as a part of the human body adjacent the apparatus 2, and a shear component which is parallel to the surface such for example as the part of the human body. The pressure component of the force causes only the distance between the first part 8 and the second part 10 to be reduced, due to the deformation of the flexible members 14. This causes the distance between the first capacitive member 18 and the second capacitive member 20 to be reduced accordingly, and thus enables a capacitance change to be measured between the first capacitive member 18 and the second capacitive member 20, see FIG. 1d. The shear component of the force causes both the distance and the overlapping area of the first part 8 and the second part 10 to be reduced, as shown in FIG. 1e. This causes the distance and overlapping area between the first capacitive member 18 and the second capacitive member 20 to be reduced accordingly. This enables a capacitance change to be measured between the first capacitive member 18 and the second capacitive member 20 when parts 8, 10, 14 are made of insulating materials. When the first part 8 and the second part 10 are made of conductive materials such for example as conductive polymers or metals, the capacitance change can be measured between parts 8 and 10. In this case, the flexible members 14 should be made of an insulating material such for example as a thermoplastics material or a photopolymer material so that the capacitor can be formed between parts 8 and 10 and thus capacitance change between parts 8 and 10 can be measured accordingly.

When the first and second parts 8, 10 and the inner flexible means 12 are all made as a flexible insulating structure, the first and second capacitive members 18, 20 are respectively positioned on the first and second parts 8, 10 in order to form conductive electrodes for capacitance. The capacitance between the first and second capacitive members 18, 20 is then able to be used to detect the pressure and shear forces based on the same principal as described above. The first and second capacitive members 18, 20 can be of the same conductive material or different conductive materials. The first and second capacitive members 18, 20 may be such that they cover all of the first and second parts 8, 10, or they may be patterned according to design requirements. The first and second capacitive members 18, 20 can be attached to the first and second parts 8, 10 using PCB techniques, for example by attaching thin copper foils to top and bottom plates. The conductive layers can be formed into any patterns required to enable various transduction mechanisms, for example electrostatic, electromagnetic, electrothermal, piezoresistive, or piezoelectric. The changes in capacitance can be directly detected using any appropriate electrical circuitry (not shown). To this end, the apparatus 2 may form part of an electrical oscillator circuit such for example as a resonant circuit that uses an inductor and a capacitance, where changes of capacitance are able to be reflected by the frequency change of the oscillators.

The materials for the first and second parts 8, 10 and the inner flexible means 12 can be the same or different. The inner flexible means 12 can be a continuous solid layer, or the inner flexible means 12 can be a layer containing a plurality of flexible members such as those shown as the flexible members 14. The inner flexible means 12 can also be a layer with flexible members 14 embedded in a continuous layer, for example, a layer containing a plurality of flexible members 14 with the gaps among them filled with other materials. The first and second capacitive members 18, 20 may be formed using forming techniques such for example as sputtering, electrochemical deposition, inkjet printing, additive manufacturing methods, or by attaching thin copper foils as used in the production of flexible PCBs. If patterns are required to be formed in the first and second capacitive members 18, 20, then shadow masks may be used during the deposition process. Non-flexible PCBs can also be used for the capacitive members 18 and/or 20. Non-flexible PCBs with insulating substrates can also be used to replace the combination of the parts 8 and 18 and/or the combination of the parts 10 and 20.

Figure 2A:
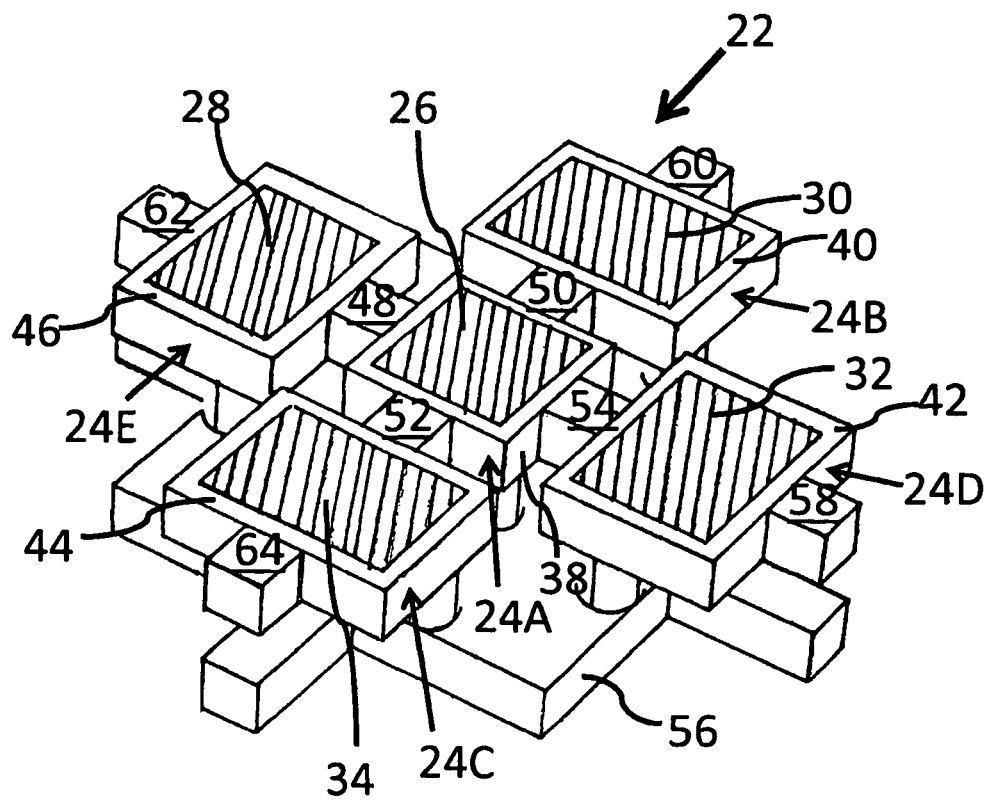
FIG. 2a is a perspective view from above of second apparatus of the present invention.
Figure 2B:
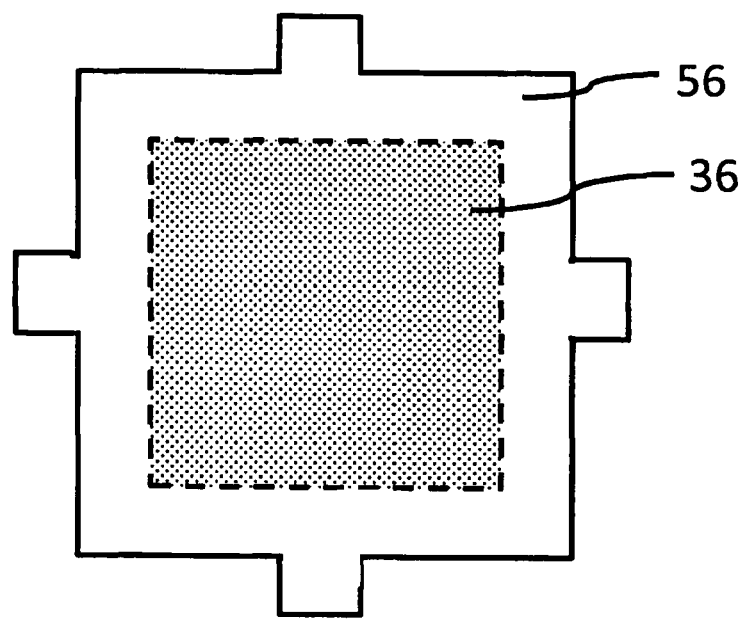

Referring now to FIGS. 2a and 2b, there is shown in FIG. 2a apparatus 22 of the present invention. The apparatus 22 comprises five capacitance units 24A-24E as shown. Each capacitance unit 24A-24E comprises a flexible means which may be the same or different from the flexible means 4 shown in the apparatus 2 of FIG. 1a. The capacitance units 24A-24E may be manufactured using 3D printing by a 3D printer. Alternatively, the capacitance units 24A-24E may be manufactured using elastomer material which is moulded to shape. All the illustrated parts are insulating, except for top conductive electrodes 26, 28, 30, 32 and 34, and a common bottom conductive electrode 36 as shown in FIG. 2b. The top conductive electrodes 26, 28, 30, 32, 34 are situated on top plates 38, 40, 42, 44 and 46 respectively. These top plates 38, 40, 42, 44, 46 can either be separated or they can be linked through linking formations 48, 50, 52, 54. The capacitance units 24A-24E all have the same bottom conductive electrode 36. This common bottom conductive electrode 36 is formed on a common bottom plate 56.

The bottom conductive electrode 36 completely overlaps with the central top conductive electrode 26, but only partially overlaps with the peripheral top conductive electrodes 28, 30, 32, 34. This overlap area may be defined as "A". For the central unit 24A having the top conductive electrode 26, the capacitor electrodes are electrodes 26 and 36. Normal pressure results in a gap change ($\Delta d$) between the capacitor electrodes 26 and 36. The gap change results in a capacitance change in the central capacitance unit 24A.

A combination of pressure and X-direction shear load results in both $\Delta d$ and $\Delta A$ for the capacitance unit 24B having the top conductive electrode 30, and the capacitance unit 24C having the top conductive electrode 34. This leads to a differential change of capacitance for these capacitance units 24B and 24C. The X-direction shear can also be measured by one capacitance unit and/or a combination of the units along that direction, for example, unit 24B or unit 24C or a combination of units 24B and 24C.

By subtracting the pressure contribution obtained from the capacitance unit 24A having the top conductive electrode 26 (through electrical signal and/or software processing), an x-direction shear component can be obtained through signals from the capacitance units 24B or 24C or combination of units 24B and 24C. A Y-directional shear load can be detected through units 24D or 24 E or combination of units 24D and 24E based on a similar principal. The apparatus 22 can work alone or it can form a sensor network comprising multiple sensors which are able to be linked into arrays using arms 58, 60, 62, 64 as shown in FIG. 2a, in order to provide mapping over a large area.

Figure 3A:
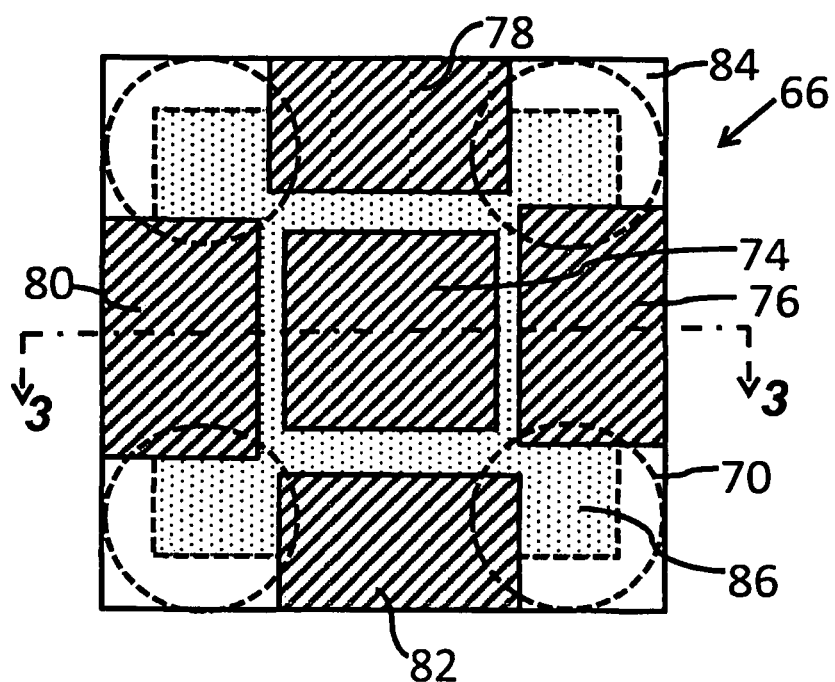
FIG. 3a is a top plan view of third apparatus of the present invention.
Figure 3B:
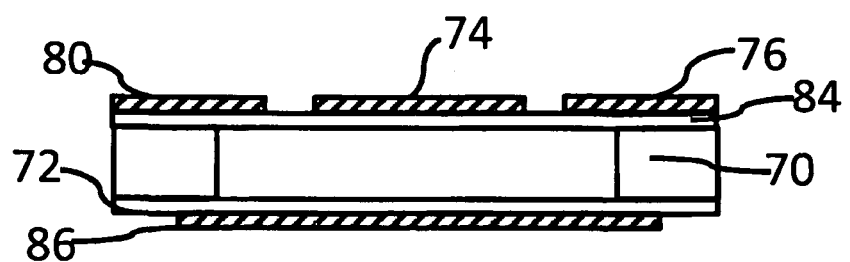

Referring now to FIGS. 3a and 3b, there is shown apparatus 66 comprising five capacitive units as shown in FIG. 3a. Parts 70, 72, 84 are formed to be insulating. Top conductive electrodes 74, 76, 78, 80, 82 are supported by a common plate 84. A bottom conductive electrode 86 is situated on the part 72 which is an insulating plate.

The electrode 74 completely overlaps the bottom conductive electrode 86 to form a pressure sensing capacitor. The electrodes 76, 78, 80, 82 partially overlap the bottom conductive electrode 86, and thereby act as X- and Y-direction shear loads respectively. X and Y direction shear loads can be detected by using one top electrode or two top electrodes. For example, while the bottom electrode 86 is used for the common bottom electrode, for X-direction shear detection, the top capacitance electrode 76 or 80 or a combination of the top capacitance electrodes of 76 and 80 can be used. For Y-direction shear detection, the top capacitance electrode 78 or 82, or a combination of the top capacitance electrodes 78 and 82 can be used.

The part 70 is a supporting flexible structure which can be produced in various dimensions and shapes. The part 70 can be a continuous layer made of materials which are the same as, or different from, the materials used for the parts 72 and 84.

Figure 4A:
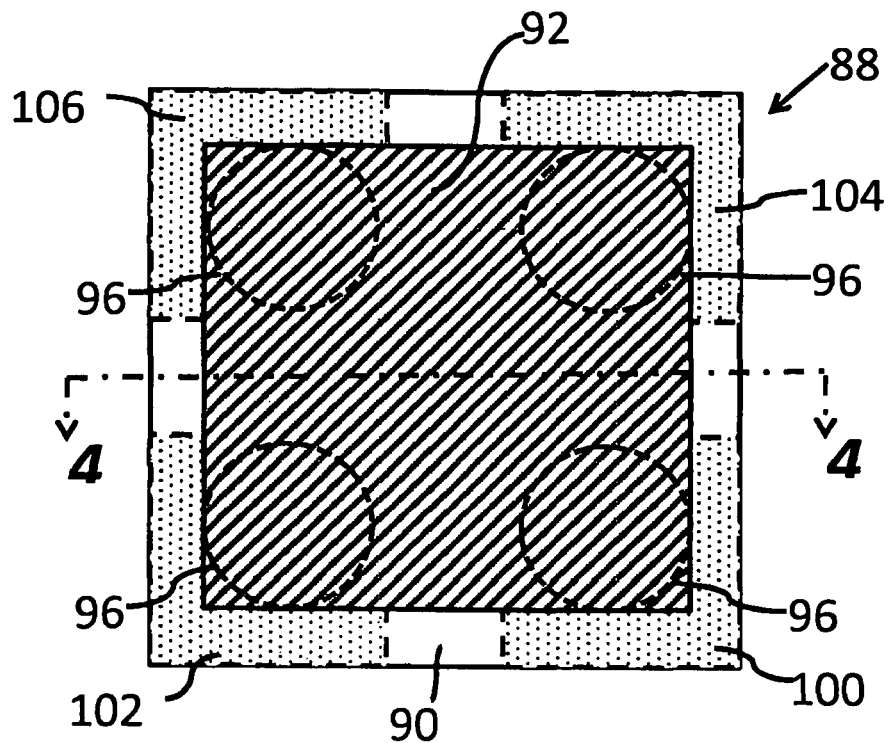
FIG. 4a is a top plan view of fourth apparatus of the present invention.
Figure 4B:
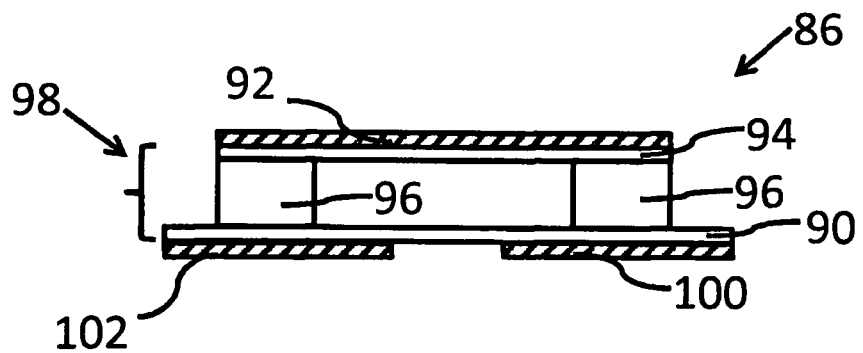

Referring now to FIGS. 4a and 4b, there is shown apparatus 88 comprising five capacitive units. There are four bottom electrodes supported by a common plates 90. There is one top electrode 92 supported by a plate 94. The plates 90, 94 are separated by flexible means in the form of supporting pillars 96. The shape and dimensions of the pillars 96 may be varied as desired. The plates 90, 94 and the pillars 96 form a sensing structure 98 which is produced by 3D printing using a 3D printer.

The top electrode 92 partially overlaps with bottom electrodes 100, 102, 104, 106. A capacitor is formed by the top electrode 92 and the joint bottom electrodes 100, 102, 104, 106 to detect a pressure load normal to the contacting surface. This is because the capacitance of this capacitor only changes with the distance between the top and bottom electrodes, which is used to reflect pressure load. Individual capacitors formed by the top electrode 92 and the bottom electrodes 100, 102, 104, 106 respectively can be used to detect X- and Y-direction shear loads. Again this apparatus can also comprise three capacitive units, with a pressure detection unit being formed between the top electrode 92 and joint bottom electrodes, while X, Y-direction shear loads are detected, for example by using the bottom electrodes 100 and 104 respectively.

In a further embodiment of the invention, the five capacitive units described above with reference to FIGS. 3a and 3b or the five capacitive units described above with reference to FIGS. 4a and 4b, can be such that the top and bottom conductive layers can be patterned as electrodes, and also be patterned to form electrical circuit connections to link the relevant electrodes if required.

In a further embodiment, for use for electrical signal processing, the capacitance of each capacitor unit can be detected through capacitance measurement. Also, the variation of capacitance can be detected using any appropriate electrical circuitry (not shown) including using oscillator electrical circuitry, i.e. a resonant circuit that uses an inductor and a capacitor, and where changes of capacitance are able to be reflected by using the frequency change of the oscillators.

Figure 5:
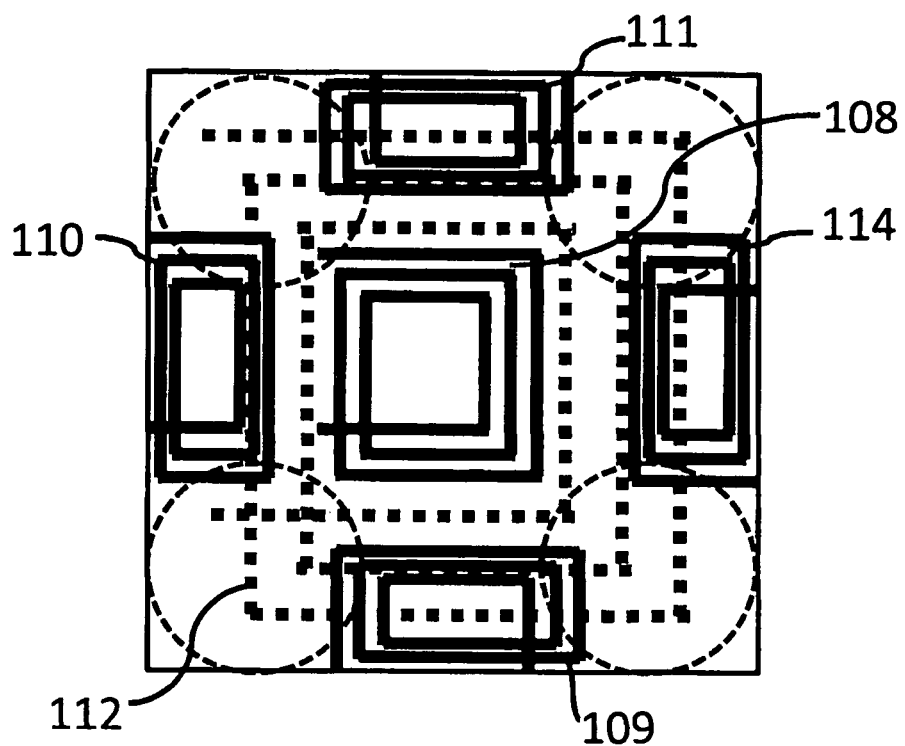
FIG. 5 is a top plan view of fifth apparatus of the present invention.

The apparatus of the present invention may utilise inductive transducer means instead of capacitive transducer means. More specifically, the apparatus utilising the inductive transducer means may be based on the apparatus 2 shown in FIG. 1, but with the first and second capacitive members 18, 20 formed into coil shapes to form an electromagnetic inductive device. Such an electromagnetic inductive device is shown by way of example in FIG. 5. In FIG. 5, each sensor unit has five pairs of electromagnetic induction devices. For this apparatus, each sensor unit can also have three pairs of electromagnetic induction devices.

All of the different types of apparatus shown in FIGS. 2, 3 and 4 can also be adapted for inductive sensing mechanisms, simply by replacing the top and bottom conductive members 18, 20, i.e. electrodes, in FIGS. 2, 3 and 4 with coil shapes. In this way, five inductive pairs instead of capacitance pairs are formed. Apparatus comprising three inductive pairs can also be formed.

For each inductive pair, the common bottom coil 112 is the driving coil and the top coils 108, 109, 110, 111, 114 are the measuring coils respectively. For example and referring to FIG. 5, for the middle pair of coils 108, 112, current is applied to the coil 112 which generates a localised magnetic field. Some of the generated magnetic flux passes through the middle coil 108. When the coil 108 and the coil 112 are brought closer together, by pressure normal to the contacting surface, the flux passing through the coil 108 changes. This leads to voltage detection by coil 108. For the inductive device formed by the coil 114 and the coil 112, for example, part of the flux generated from the coil 112 passes through the coil 114, and any shear force will alter the overlapping area between the coil 112 and the coil 114. Thus, the amount of flux going through the coil 114 will enable voltage detection by the coil 114. In this way, both pressure and shear can be detected by an electromagnetic inductive device derived from FIG. 5.

With reference to FIGS. 1-5, the sensing structures in the apparatus of the present invention may be formed by 3D printing using a 3D printer, or by using elastomer material which is moulded to shape. The sensing structures are able simultaneously to measure loads which are normal and in shear (X, Y) direction applied to the sensor apparatus, and thereby indicative of these loads as applied to an adjacent part of a surface. The apparatus of the present invention is capable of producing electric signals capable of differentiating both types of loads, or combinations thereof. This means that the three directional loads (X, Y and Z) can separately be calibrated prior to measurements. Preferably, the sensor apparatus of the present invention is capable of measuring static loads as well as dynamic loads. For example, in prosthetic socket liner and/or socket applications, after calibrations of the three directional loads, when a static load is applied, pressure and/or shear load information can be obtained using the apparatus. Equally, for example with two surfaces in the form of a part of a human body and external support surface, when an amputee is walking or moving, a dynamic change of loads can also be measured using the apparatus of the present invention.

Figure 6:
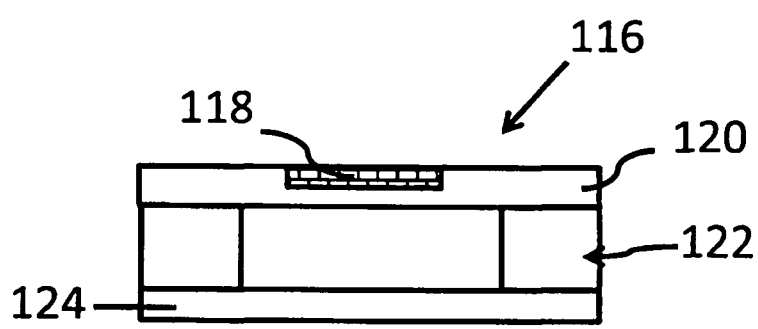
FIG. 6 is an end view of sixth apparatus of the present invention, the apparatus utilising a signal-processing integrated circuit chip housed in an indent in a sensing structure which forms part of the apparatus.

Electrical signals provided by the apparatus of the present invention may be processed and monitored using one or more integrated circuit chips. The IC chips may be programmed for specific signal process requirements. Appropriate IC chips can be embedded in the insulating flexible means as shown by way of example in FIG. 6. In FIG. 6, there is shown apparatus 116 having an IC chip 118 embedded in a layer 120. The apparatus 116 also includes flexible members 122 which are electrically insulating, and a lower layer or plate 124. When the layers 120, 124 are not conductive, then conductive layers can be attached on top of the layers 120, 124 to enable transduction from mechanical deformation to electrically detectable signals.

Figure 7:
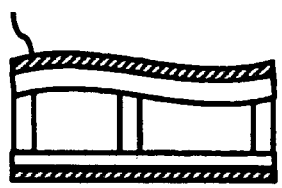
FIG. 7 is a schematic edge view of individual apparatus as shown in FIG. 1a when one of the contacting surfaces are non-planar.
Figure 8:
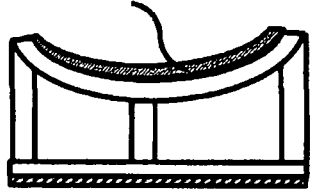
FIG. 8 is a schematic edge view of an individual apparatus shown in FIG. 1a when one of the contacting surfaces is a concave surface.
Figure 9:
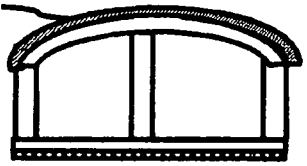
FIG. 9 is a schematic edge view of an individual apparatus shown in FIG. 1a when one of the contacting surfaces is a convex surface.

It will be appreciated from the above description with reference to FIGS. 1-5 that the apparatus of the present invention can be both planar or non-planar shapes. FIGS. 7, 8 and 9 show how examples of individual sensing apparatus can be non-planar to allow conformal contact to the sensing surface with various forms of curves. The flexible means can both be non-planar. These types of apparatus may be formed by 3D printing using a 3D printer or using elastomer material. The shaped surfaces 121, 123 and 125 can be adapted at the design stage. Scanned CAD models of the applicable external surface an be input into the designs with all kinds of surface shapes, which can then be printed out by 3D printing.

Figure 10:
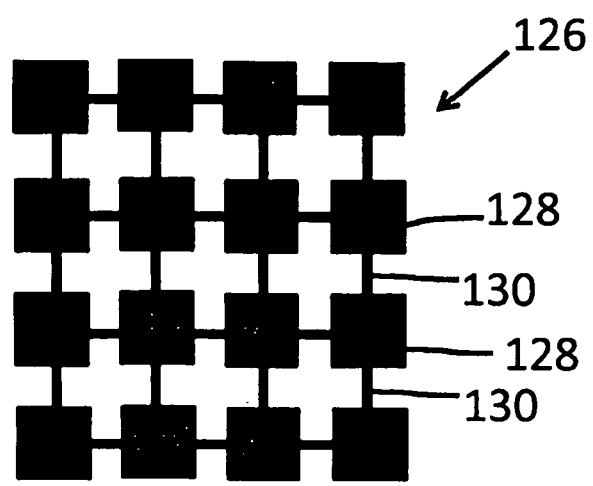
FIG. 10 is a top plan view showing how individual units of the apparatus of the present invention are able to be interconnected to form a sensor network.

Referring now to FIG. 10, there is shown how sensor apparatus of the present invention can be interconnected into sensor networks in order to provide a mapping capability. More specifically, FIG. 10 shows a sensor network 126 formed of a plurality of units of sensor apparatus 128 linked by links 130. The networks comprising connected units of the apparatus can be formed by 3D printing using a 3D printer.

Figure 11:
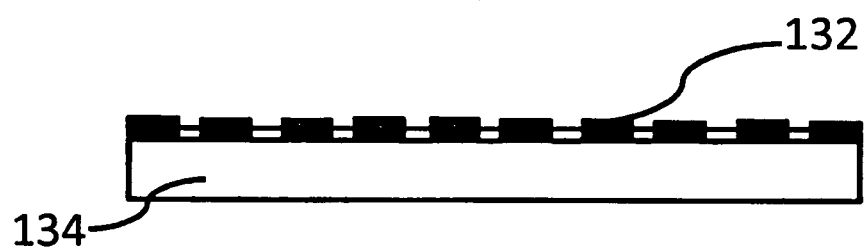
FIG. 11 is a schematic end view showing a sensor network applied to a surface in the form of a planar surface.

FIG. 11 illustrates how the surface of a network 132 can be planar to accommodate a flat surface 134. The networks comprising the connected units of the apparatus can be formed by 3D printing using a 3D printer, or by using elastomer material which is moulded to shape.

Figure 12:
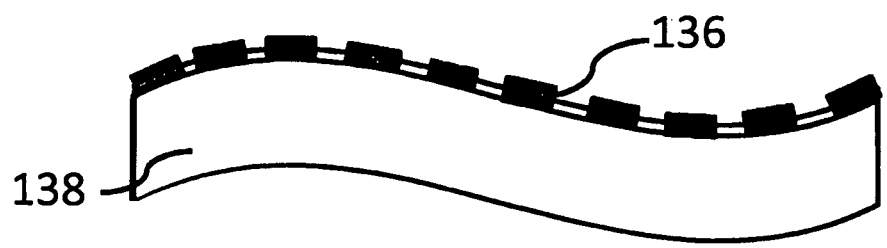
FIG. 12 is a schematic side view showing a sensor network applied to a surface in the form of a non-planar surface.

FIG. 12 shows how a network 136 may be non-planar of any suitable and appropriate shape, in order to accommodate a curved surface 138. The networks comprising the connected units of the apparatus can be formed by 3D printing using a 3D printer, or by using elastomer material which is moulded to shape.

The curved surface device 138 may be any concave or convex surface, or combination of concave and convex surfaces. In order to achieve a required configuration, the interconnected flexible units for the network 136 may be formed by 3D printing according to a CAD model of the applicable external surface such for example as that illustrated by the curved surface 138. This provides conformal coverage of specific measuring areas and thus load mapping.

Typical examples of a curved surface device 138 are a prosthetic socket, seating, or an insole, outer sole or shell/upper for footwear.

Figure 13:
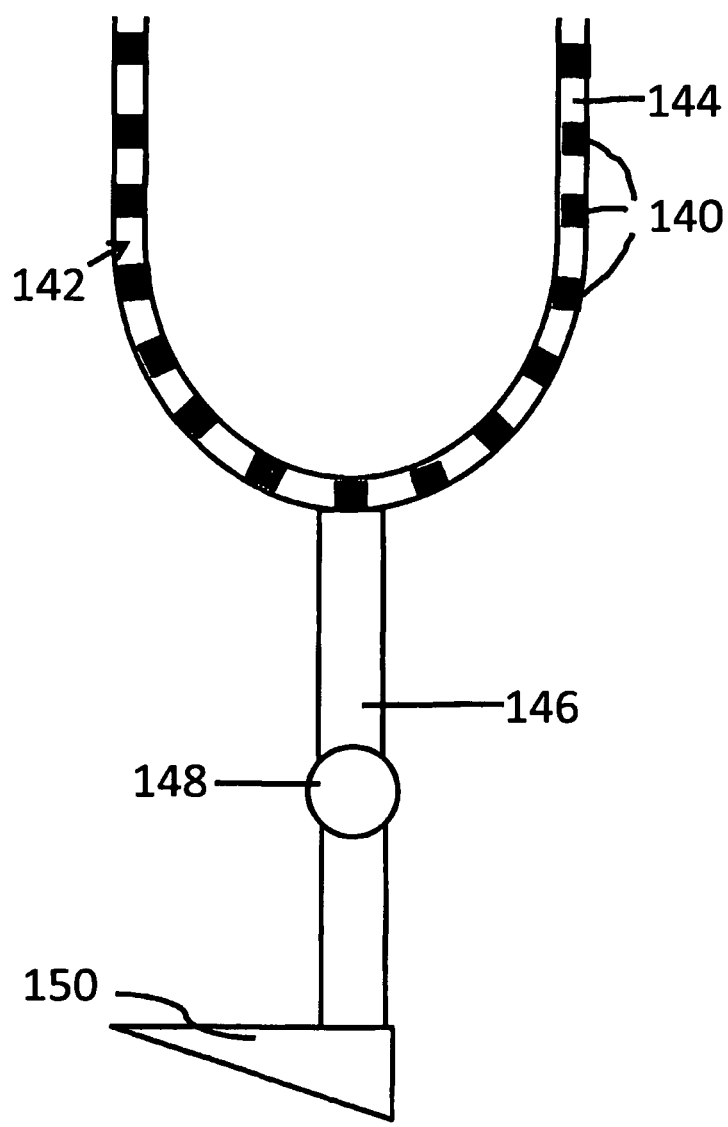
FIG. 13 shows a sensor network applied to a surface in the form of a socket wall of a prosthetic limb.

FIG. 13 illustrates how apparatus of the present invention can be applied to a prosthetic socket 142 to measure loads which are in a normal direction (giving pressure) and in a parallel direction (giving shear), respectively, in relation to the local socket surface. As shown in FIG. 13, individual sensor units of apparatus 140, or alternatively one or more sensor networks, are inserted into the wall 144 or any other areas of the prosthetic socket 142. This is accomplished by first drilling holes in the socket wall 144, and then inserting the apparatus 140 or the sensor networks into the drilled holes. The prosthetic socket 142 shown in FIG. 13 is mounted on a leg 146 having an artificial knee joint 148 and an artificial foot 150. Both individual sensor units of apparatus 140, or its associated networks, may be formed by 3D printing.

Figure 14:
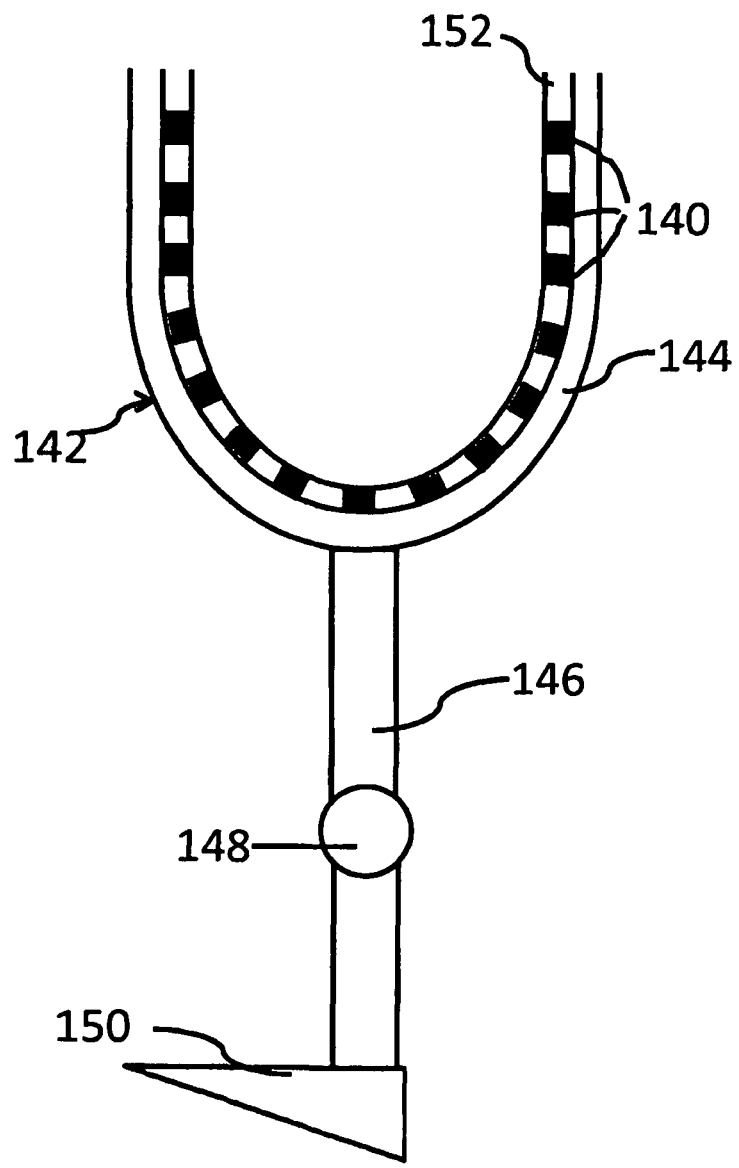
FIG. 14 shows a sensor network integrated into a surface in the form of a socket liner in a socket of a prosthetic limb.

FIG. 14 shows an arrangement similar to FIG. 13. Similar parts have been given the same reference numerals for ease of comparison and understanding. In FIG. 14, the individual units of apparatus 140, or alternatively networks comprising one or more units of apparatus 140, are inserted or integrated in a prosthetic socket liner 152 within the socket wall 144 or any components adjacent to the prosthetic socket liner 152. Both individual sensor units of apparatus 140, or its associated networks, may be formed by 3D printing, or by using elastomer material which is moulded to shape.

Figure 15:
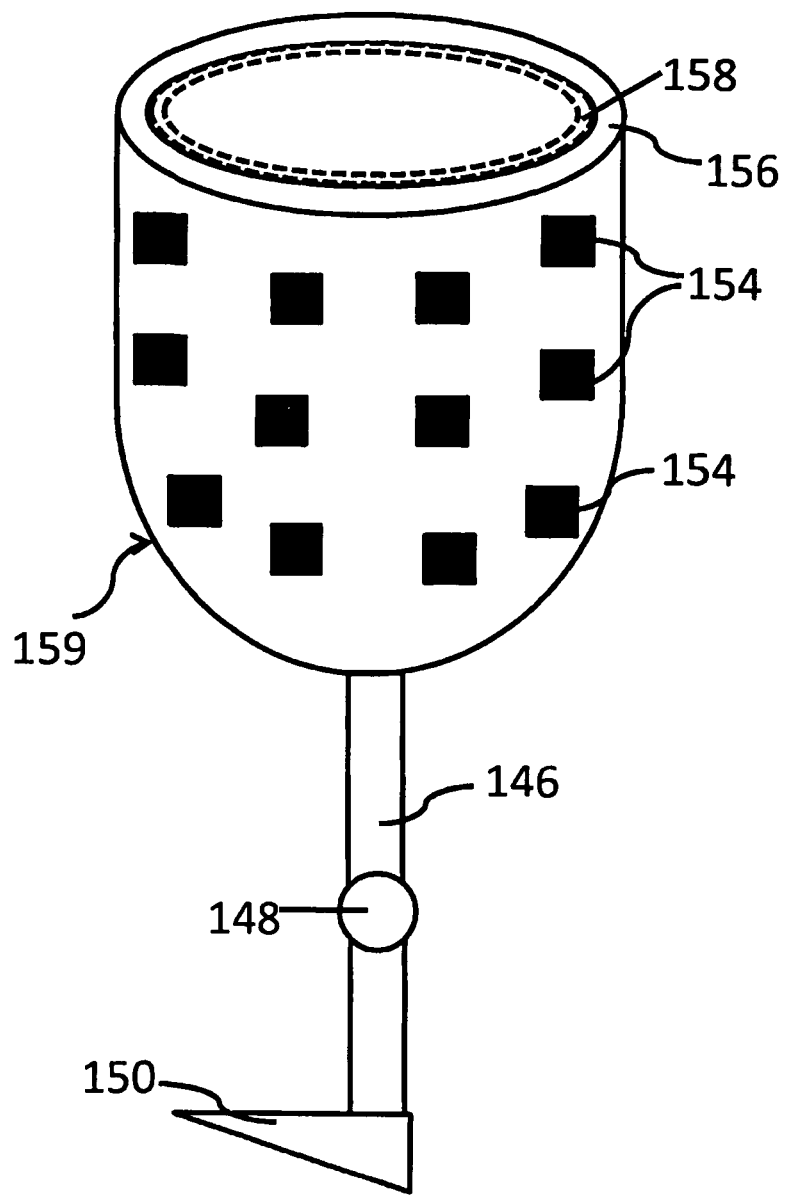
FIG. 15 shows a sensor network as it may be applied to a surface in the form of a prosthetic socket or a socket liner, and in order to provide pressure and/or shear mapping.

FIG. 15 illustrates how individual units of sensor apparatus 154, or networks of such apparatus, can be positioned in a socket wall 156 or a socket liner 158 of a prosthetic socket 159 to provide load mapping of the relevant area. For sensor networks, the interconnected flexible individual units of sensor apparatus 154 are able to be formed by 3D printing according to a CAD model of the prosthetic socket 159, and thereby be able to accommodate different shapes of individual sockets. Both individual sensor units of apparatus 154, or its associated networks, may be formed by 3D printing.

The apparatus of the present invention may be used to optimise and facilitate prosthetic socket fitting, and also to aid the design of prosthetic sockets. The apparatus may be used to aid other parts of prosthetic fitting, for example alignment, set up, etc.

Figure 16:
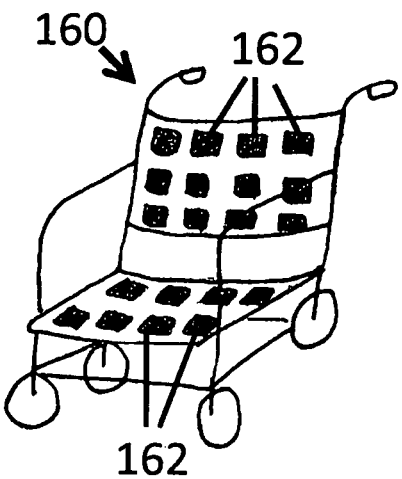
FIG. 16 shows the apparatus of the present invention in use on a wheelchair.

FIG. 16 shows a wheelchair 160 provided with apparatus 162 of the present invention.

Figure 17:
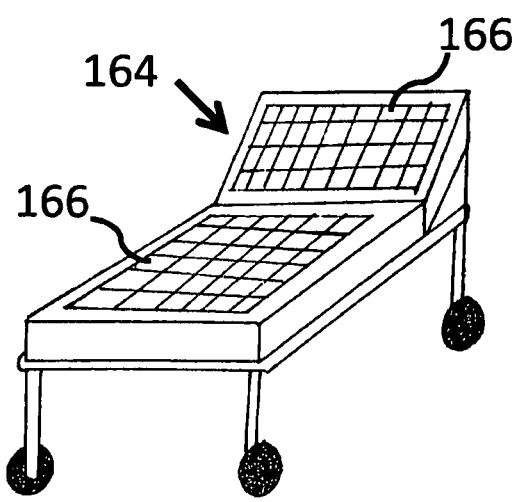
FIG. 17 shows the apparatus of the present invention in use on a hospital bed.

FIG. 17 shows a hospital bed 164 provided with apparatus 166 of the present invention.

Figure 18:
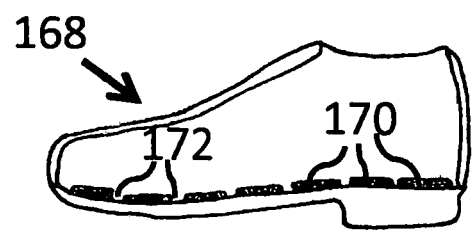
FIG. 18 shows the apparatus of the present invention in use on footwear in the form of a shoe.

FIG. 18 shows footwear 168 provided with apparatus 170 of the present invention. The apparatus 170 is advantageously provided in an insole 172 of the footwear 168.

The wheelchair 160, the hospital bed 164 and the footwear 168 shown in FIGS. 16, 17 and 18 are such that the apparatus 162, 166, 170 respectively is able to provide local load information, while their connected networks can provide load mapping over whole areas. The illustrated interconnected flexible units of the apparatus 162, 166, 170 form sensor networks. These networks can be formed by 3D printing using a CAD model of the applicable external surfaces, for example in order to ensure intimate contact between the apparatus of the present invention and a part of a human body.

Figure 19:
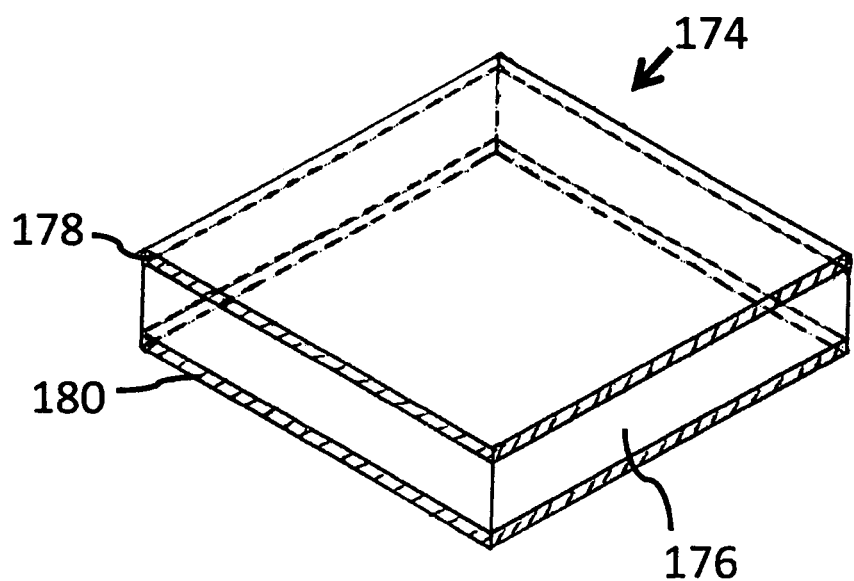
FIG. 19 shows in outline form, the principle of construction of apparatus of the present invention with a solid continuous flexible means.

Referring now to FIG. 19, there is shown apparatus 174 of the present invention. The apparatus 174 is like the apparatus 2 shown in FIG. 1. The apparatus 174 is such that it has a solid continuous flexible means 176 with first and second electrode parts 178, 180.

Figure 20:
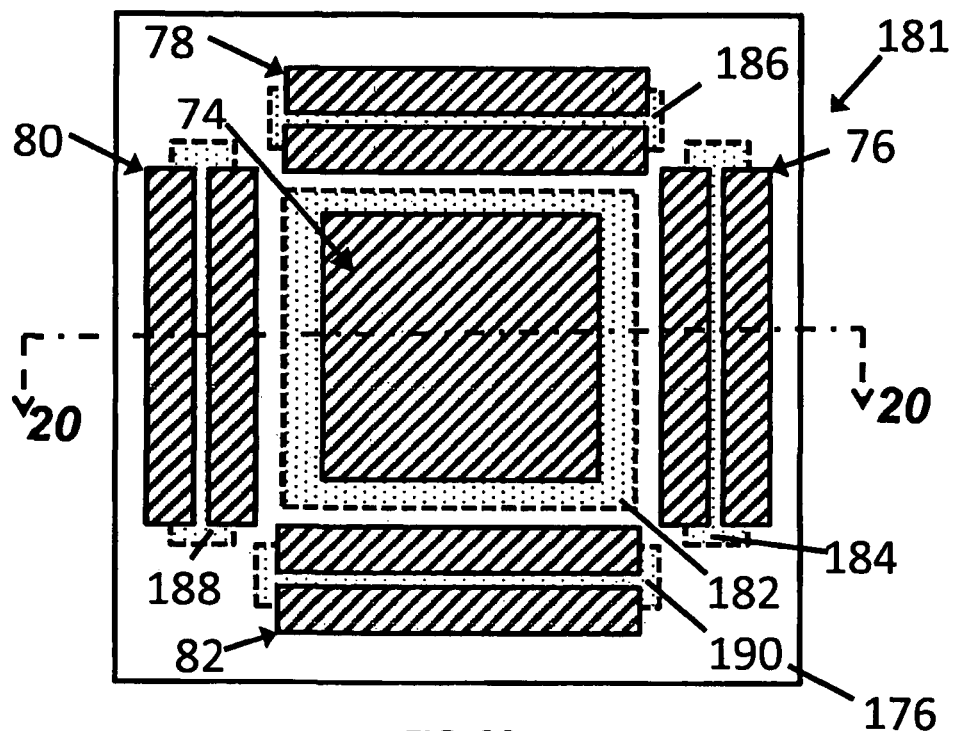
FIG. 20 is a top plan view showing in detail the construction of further apparatus of the present invention.
Figure 21:
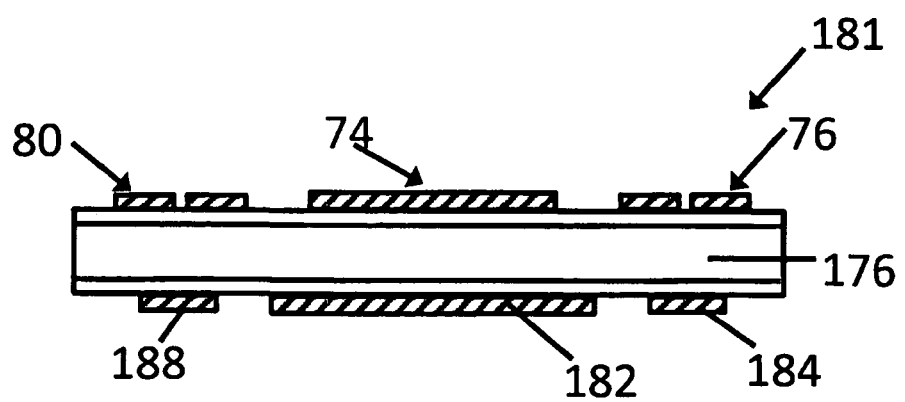
FIG. 21 is a cross section on the line 20-20 shown in FIG. 20.

Referring now to FIGS. 20 and 21, there is shown apparatus 181 which is like the apparatus 66 shown in FIGS. 3*a* and 3*b*. The electrode part 178 has five separated conductive electrodes 74, 76, 78, 80, 82 similar to those shown in FIG. 3*a*. The electrode part 180 also contains five conductive electrodes 182, 184, 186, 188, 190. For each conductive electrode 76, 78, 80, 82 there are two differential electrodes which partially overlap with the relevant bottom electrode. For example taking electrode 76, the top two electrodes partially overlap the bottom electrode. These electrodes are used to sense directional shear force. The top two electrodes for electrodes 76 provide differential capacitance change under X-directional shear.

It is to be appreciated that the embodiments of the present invention described above with reference to the accompanying drawings have been given by way of example only and that modifications may be effected. Thus, for example, the apparatus of the present invention may be included in a closed loop control system which can activate relevant actuators based on signals from the sensing apparatus or networks. Shapes of the entire apparatus of the invention and also component parts of the apparatus of the present invention may be symmetrical or non-symmetrical in all directions. Individual components shown in the drawings are not limited to use in their drawings and they may be used in other drawings and in all aspects of the invention.

The invention claimed is:

1. Apparatus for sensing and measuring pressure and shear components of a force at an interface between two surfaces, which apparatus comprises:
   (i) at least one flexible means for receiving the pressure component of the force and the shear component of the force; and
   (ii) transducer means for producing electrical signals consequent upon movement of the flexible means in response to the pressure component of the force and/or the shear component of the force,
   and the apparatus being such that:
   (iii) the transducer means comprises first and second electrode parts which are spaced apart by the flexible means;
   (iv) the first and second electrode parts move solely towards each other as a result of the pressure component of the force being applied to the flexible means;
   (v) the first and second electrode parts move towards and parallel to each other as a result of the shear component of the force being applied to the flexible means; and
   (vi) the movement of the first and second electrode parts towards and parallel to each other is such that:
   (a) the movement has an X-direction component due to the shear component of the force having an X-direction; and
   (b) the movement has a Y-direction component due to the shear component of the force having a Y-direction.

2. Apparatus according to claim 1 in which the sensing structure is one that has been produced by 3D printing using a 3D printer, or by using elastomer material which is moulded to shape.

3. Apparatus according to claim 1 and which is integral with at least one sensing pad for use within a prosthetic socket liner or a prosthetic socket.

4. Apparatus according to claim 1 in which at least one of the first and second electrode parts has a planar surface.

5. Apparatus according to claim 1 in which at least one of the first and second electrode parts includes at least one flexible printed circuit board.

6. Apparatus according to claim 1 in which the flexible means is an elastomer, silicone, a thermoplastic elastomer or urethane.

7. Apparatus according to claim 1 in which the flexible means has a planar surface.

8. Apparatus according to claim 1 in which the flexible means is an insulating sensing structure, and in which the transducer means comprises conductive layers which are provided on the flexible means and which enable the production of an electrical signal.

9. Apparatus according to claim 1 in which the flexible means are flexible pillar members.

10. Apparatus according to claim 1 in which the transducer means is a capacitive transducer means.

11. Apparatus according to claim 10 in which the capacitive transducer means comprises a first capacitive member on a first surface of the flexible means, and a second capacitive member on a second surface of the flexible means.

12. Apparatus according to claim 11 in which the first capacitive member is a member with planar or non-planar surfaces, and in which the second capacitive member is a member with a planar surface.

13. Apparatus according to claim 11 in which the first capacitive member is a member with planar or non-planar surfaces, and in which the second capacitive member is a member with a non-planar surface.

14. Apparatus according to claim 1 in which the transducer means is an inductive transducer means.

15. Apparatus according to claim 14 in which the inductive transducer means comprises a first inductive member on a first surface of the flexible means, and a second inductive member on a second surface on the flexible means.

16. Apparatus according to claim 1 and including at least one signal processing integrated circuit.

17. Apparatus according to claim 1 and including a plurality of the flexible means.

18. An article when provided with apparatus according to claim 1.

19. An article according to claim 18 and in the form of a prosthesis, a wheelchair, a bed, or footwear.

20. An article according to claim 19 which is in the form of the prosthesis, and in which the apparatus is in the form of a prosthetic socket liner, or at least one sensing pad in a prosthetic socket of the prosthesis.

21. An article according to claim 18 and including a closed loop control system for activating relevant actuators in response to signals from apparatus according to claim 1.

22. Apparatus according to claim 1 in which at least one of the first and second electrode parts has a non-planar surface.

23. Apparatus according to claim 1 in which the flexible means has a non-planar surface.

\* \* \* \* \*